US00PP28519P2

(12) United States Plant Patent
Oudolf

(10) Patent No.: US PP28,519 P2
(45) Date of Patent: Oct. 10, 2017

(54) ***MOLINIA* PLANT NAMED 'CRYSTAL VEIL'**

(50) Latin Name: *Molinia litoralis*
Varietal Denomination: Crystal Veil

(71) Applicant: Green Elite Collection B.V., Lisserbroek (NL)

(72) Inventor: Piet Oudolf, Hummelo (NL)

(73) Assignee: GREEN ELITE COLLECTION BV, Lisserbroek (NL)

( * ) Notice: Subject to any disclaimer, the term of this patent is extended or adjusted under 35 U.S.C. 154(b) by 0 days.

(21) Appl. No.: 14/999,572

(22) Filed: May 26, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Penny J. Aguirre

(57) ABSTRACT

A new cultivar of *Molinia*, 'Crystal Veil', that is characterized by its tall plant height of 200 cm and flower spikes that are fine in texture.

1 Drawing Sheet

Botanical classification: *Molinia litoralis.*
Varietal denomination: 'Crystal Veil'.

BACKGROUND OF THE INVENTION

The present invention relates to a new and distinct cultivar of *Molinia litoralis* and will be referred to hereafter by its cultivar name, 'Crystal Veil'. 'Crystal Veil' represents a new cultivar of herbaceous perennial, an ornamental grass grown for landscape use.

The Inventor discovered the new cultivar, 'Crystal Veil', as a chance seedling in the Inventors garden in Hummelo, Netherlands in the summer of 2010. Although the parentage is unknown, *Molinia litoralis* 'Transparent' (not patented) is thought to be a likely parent based on the characteristics of 'Crystal Veil' and its proximity in the same growing area.

Asexual propagation of the new cultivar was first accomplished by division in Hummelo, Netherlands in 2012 by the Inventor. Asexual propagation by division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Crystal Veil' as a unique cultivar of *Molinia.*

1. 'Crystal Veil' exhibits a plant height of 200 cm.
2. 'Crystal Veil' exhibits flower spikes that are fine in texture (finer than is typical of plants of *Molinia litoralis.*

'Crystal Veil' can be most closely compared to cultivars, *Molinia litoralis* 'Transparent' (not patented) and *Molinia litoralis* 'Skyracer' (not patented). 'Transparent' differs from 'Crystal Veil' in having flower spikes that are larger in size and finer in texture and in having a taller and more arching plant habit. 'Skyracer' differs from 'Crystal Veil' in having a taller plant height and in having a more upright plant habit.

BRIEF DESCRIPTION OF THE DRAWING

The accompanying photograph were taken in October and illustrate the characteristics of 4 year-old plants as grown in a garden in Hummelo, Netherlands. The photograph 1 provides a side view of 'Crystal Veil'. The colors in the photographs are as close as possible with the digital photography techniques available, the color values cited in the detailed botanical description accurately describe the colors of the new *Molinia.*

DETAILED BOTANICAL DESCRIPTION

The following is a detailed description of one-year-old plants of the new cultivar as grown in two-gallon containers in Rougemont, N.C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—August to September in The Netherlands.
*Plant type.*—Herbaceous perennial grass.
*Plant habit.*—Low clump of foliage with tall flowering spikes held upright and slightly cascading.
*Height and spread.*—Reached an average of 200 cm in height and 50 cm in spread.
*Cold hardiness.*—At least in U.S.D.A. Zone 4.
*Diseases.*—No resistance to susceptibility to diseases has been observed.
*Root description.*—Fibrous, fine, 161D in color.
*Propagation.*—Division.
*Growth rate.*—Moderate.

Culm (stem) description:

*General.*—Slightly oval, solid pith, thin but strong, erect.
*Culm number.*—An average of 9 flowering culms and 16 shorter none flowering culms in a 2-gallon container, forming tight clump.
*Culm color.*—137D in summer, 161D in fall and winter.

*Culm size*.—Average of 2 mm in diameter, averaging 100 cm in height from the base to the tip of the flower panicle and an average of 3 cm on non-flowering culms.

*Culm surface*.—Glabrous.

*Internode length*.—An average of 4 cm.

Foliage description:

*Leaf shape*.—Narrowly lanceolate.

*Leaf division*.—Simple.

*Leaf margin*.—Entire.

*Leaf base*.—Sheathed to base of culm.

*Leaf apex*.—Sharply attenuate.

*Leaf venation*.—Parallel, not distinguishable in color from leaf.

*Leaf width*.—Average of 1 cm at widest section.

*Leaf length*.—Blade; an average of 30 cm, sheathed portion; 8 to 15 cm.

*Leaves per culm*.—Average of 3 on flowering culms, average of 4 on non-flowering culms.

*Leaf surface*.—Glabrous and dull on both surfaces.

*Ligule*.—0.5 mm in width, comprised of a moderate amount of soft hairs about 1.5 mm in length and NN155C in color on inner surface.

*Leaf color* (*both surfaces*).—Summer; 137C, fall and winter 161B.

Flower description:

*Inflorescence type*.—Airy panicle of racemes at terminus of stem, primarily symmetrical.

*Inflorescence size*.—Panicle; an average of 35 cm in length and 13 cm in width, racemes; an average of 8 cm in length and 3 cm in width.

*Spikelet description*.—Average of 150 per panicle, awnless, glumes; 2 mm in length and width, 145C in color with stripes of 137B, convex, glabrous surface, lemmas; 2, 3.5 mm in length and 1.5 mm in width, convex, glabrous surface, 145D in color with stripes of 137B, palea; 4 mm in length and 1.5 mm in width, a blend of 145D and 155B in color, convex, glabrous surface.

*Spikelet size*.—About 4 mm in length and 2 mm in width (excluding reproductive organs).

*Rachis*.—An average of 54 cm from last leaf, panicle portion an average of 35 cm in length and 1 to 2 mm in width with branches an average of 6.5 cm in length and 0.5 mm in width, glabrous surface, 137D in color, spikelet pedicel an average of 4 mm in length, wiry, 137D in color, glabrous surface, internode length of racemes ranges from 7 mm to 5 cm.

Reproductive organs:

*Androecium*.—Anthers; 3, 2.5 mm in length and 1 mm in width, 162C in color, longitudinal dehiscence, very fine filament 155B in color, pollen; none observed.

*Gynoecium*.—Pistil; 1, 2 plumose stigmas on short, fine styles about 0.3 mm in length and 145D in color, stigma; 84B in color, 1.5 mm in length and 1 mm in width, ovary; 1-locular, superior, elliptic in shape, 1 mm in length, 145D in color.

*Caryopsis*.—An average of 4 mm in length and about 1.5 in width, a blend of 165A and 165C in color.

It is claimed:

1. A new and distinct cultivar of *Molinia* plant named 'Crystal Veil' as herein illustrated and described.

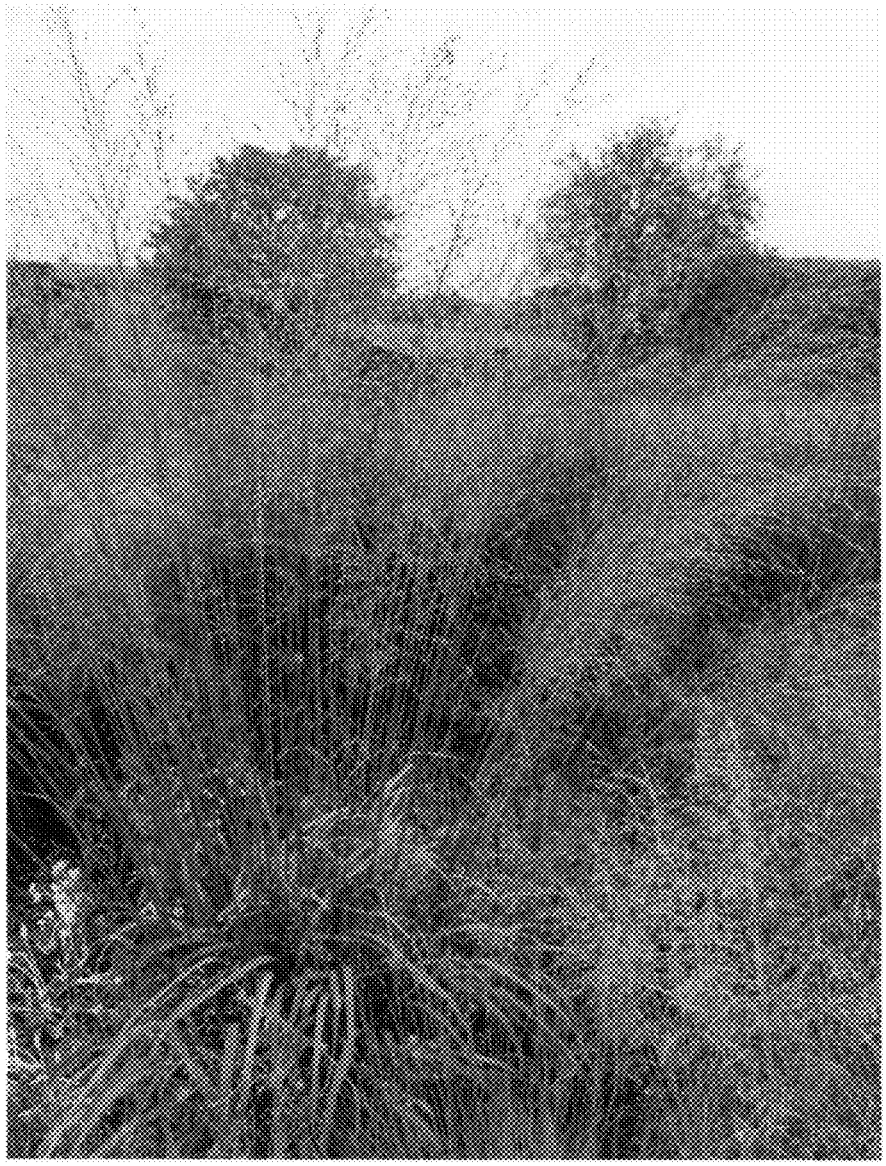

* * * * *